United States Patent [19]
Thompson

[11] Patent Number: 5,770,371
[45] Date of Patent: Jun. 23, 1998

[54] MODIFICATION OF CRYPTIC SPLICE SITES IN HETEROLOGOUS GENES EXPRESSED IN FUNGI

[75] Inventor: Sheryl Thompson, Davis, Calif.

[73] Assignee: Novo Nordisk Biotech, Inc., Davis, Calif.

[21] Appl. No.: 672,158

[22] Filed: Jun. 27, 1996

[51] Int. Cl.[6] .............................. C12Q 1/68; C12P 19/34; C12N 1/15; C07H 21/04

[52] U.S. Cl. ..................... 435/6; 435/91.4; 435/254.11; 435/320.1; 435/69.1; 536/23.1

[58] Field of Search ............................... 435/69.1, 91.1, 435/240.1, 254.11, 6, 8, 71.1, 91.4, 320.1; 530/300, 350; 536/23.1, 24.1

[56] References Cited

U.S. PATENT DOCUMENTS 5,498,531   3/1996   Jarrell .................................. 435/91.31

OTHER PUBLICATIONS

Chanfreau et al.. Interaction between the first and last nucleotides of pre–mRNA introns is a determinant of 3' splice site selection in *S. cerevisiae*. Nuc. Acids Res. vol. 22(11):1981–1987, Jun. 11, 1994.

Guo et al.. The mobile group 1 intron 3 alpha of the yeast mitochondrial COXI gene encodes a 35–kDA processed protein that is an endonuclease but not a maturase. J. Biol. Chem. vol. 270(26):15563–15570, Jul. 11, 1995.

*Primary Examiner*—David Guzo
*Assistant Examiner*—William Sandals
*Attorney, Agent, or Firm*—Steve T. Zelson, Esq.; Cheryl H. Agris, Esq.

[57] ABSTRACT

The present invention relates to methods for obtaining a fungal host cell comprising a nucleic acid sequence encoding a heterologous polypeptide, wherein at least one cryptic splice site is modified in the nucleic acid sequence. The present invention also relates to a nucleic acid sequence(s) with a modified cryptic splice site(s) as well as nucleic acid constructs, vectors, and host cells comprising said nucleic acid sequence(s). The present invention further relates to methods for recombinant production of a polypeptide encoded by said nucleic acid sequence.

25 Claims, 11 Drawing Sheets

```
ATGAGTAAAG GAGAAGAACT TTTCACTGGA GTTGTCCCAA TTCTTGTTGA ATTAGATGGC GATGTTAATG GGCAAAAATT CTCTGTTAGT GGAGAGGGTG        100

AAGGTGATGC AACATACGGA AAACTTACCC TTAAATTTAT TTGCACTACT GGGAAGCTAC CTGTTCCATG GCCAACCCTT GTCACTACTT TCTCTTATGG        200

TGTTCAATGC TTTTCAAGAT ACCCAGATCA TATGAAACAG CATGACTTTT TCAAGAGTGC CATGCCCGAA GGTTATGTAC AGGAAAGAAC TATATTTTAC        300

AAAGATGACG GAACTACAAA GACACGTGCT GAAGTCAAGT TTGAAGGTGA TACCCTTGTT AATAGAATCG AGTTAAAAGG TATTGATTTT AAAGAAGATG        400
                                                                                  |————————————— A —————————————|
                                                                                                    |—— B ——|
                                                                                                     |— C —|

GAAACATTCT TGGACACAAA ATGGAATACA ACTATAACTC ACATAATGTA TACATCATGG CAGACAAACC AAAGAATGGC ATCAAAGTTA ACTTCAAAAT        500
                                                     |———————————— D ————————————|
                                      |———————— B ————————|
                                       |—— C ——|

TAGACACAAC ATTAAAGATG GAAGCGTTCA ATTAGCAGAC CATTATCAAC AAAATACTCC AATTGGGGAT GGCCCTGTCC TTTTACCAGA CAACCATTAC        600
|— D —|
 |— C —|

CTGTCCACGC AATCTGCCCT TTCCAAAGAT CCCAACGAAA AGAGAGATCA CATGATCCTT CTTGAGTTTG TAACAGCTGC TGGGATTACA CATGGCATGG        700

ATGAACTATA CAAATAAATG TCCAGACTTC CAATTGACAC TAAAGGGATC C↑        751
```

FIG.3

95-1422
(5')TCAAGCTTTATGTCCAAGGGCGAGGAGCTCTTCACTGGAGTTGTC(3')
95-1457
(5')GATGCTCGAGTCTTGTAGTTCCCGTCATCTTTGTAAAA(3')
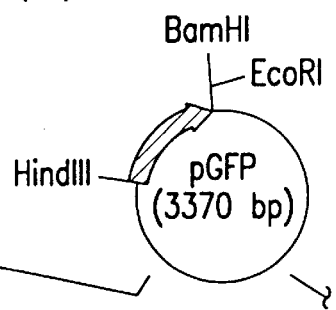
PCR AMPLIFY A PORTION OF
GFP WITH PRIMERS 95-1422
AND 95-1457.
UNTITLED-2
(341 bp)
CLONE PCR FRAGMENT
INTO pCRII
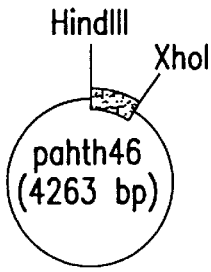
FIG.4A 95-1411
AAGACTCGAGCCGAGGTCAAGTTCGAGGGCGATACCCTTGTTAACCGCATCGAGCTCAAGGGCATTGACTTCAAGGAGGACGGC 95-1412
ACTTCAAGGAGGACGGCAACATTCTTGGCCACAAGATGGAGTACAACTATAACTCACATAACGTCTACATCATGGCCGACAAGC 95-1413
CATCATGGCCGACAAGCCAAAGAACCGCATCAAGGTTAACTTCAAGATCCGCCACAACATTAAGGACGGCAGCGTTCAGCTCCC 95-1414
CCGCAGCGTTCAGCTCGCCGACCATTATCAGCAGAACACTCCGATCGGCG 95-1415

ANNEAL OLIGONUCLEOTIDES 95-1411, 95-1412, 95-1413, 9501414 TOGETHER. PCR AMLIFY PRODUCT USING 95-1415, 95-1414.

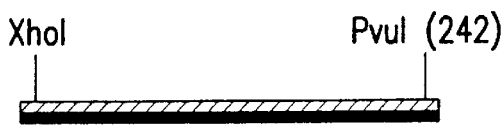

CLONE FRAGMENT INTO pCRII

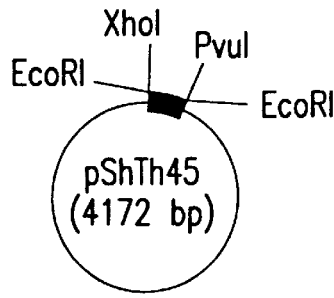

FIG.4C

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TGTCACTACT TTCTCTTATG G                2 1

( 2 ) INFORMATION FOR SEQ ID NO:2:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:2:

GTAATGGTTG TCTGGTAAAA G　　　　　　　　　　　　　　　　　　　　　　　　21

( 2 ) INFORMATION FOR SEQ ID NO:3:

( i ) SEQUENCE CHARACTERISTICS:
            ( A ) LENGTH: 41 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:3:

TATCGGCCGC ACCGGCCAAG ATGAGTAAAG GAGAAGAACT T　　　　　　　　41

( 2 ) INFORMATION FOR SEQ ID NO:4:

( i ) SEQUENCE CHARACTERISTICS:
            ( A ) LENGTH: 40 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:4:

ATACATGCAT TTATTTGTAT AGTTCATCCA TGCCATGTGT　　　　　　　　40

( 2 ) INFORMATION FOR SEQ ID NO:5:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:5:

TGTTACAAAC TCAAGAAGGA T　　　　　　　　　　　　　　　　　　　　　　21

( 2 ) INFORMATION FOR SEQ ID NO:6:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:6:

ATGAGTAAAG GAGAAGAACT TTTC　　　　　　　　　　　　　　　　　　　24

( 2 ) INFORMATION FOR SEQ ID NO:7:

( i ) SEQUENCE CHARACTERISTICS:
            ( A ) LENGTH: 85 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

```
AAGACTCGAG CCGAGGTCAA GTTCGAGGGC GATACCCTTT GTTAACCGCA TCGAGCTCAA      60
GGGCATTGAC TTCAAGGAGG ACGGC                                           85
```

(2) INFORMATION FOR SEQ ID NO:8:

(i) SEQUENCE CHARACTERISTICS:
(A) LENGTH: 83 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

```
GCTTGTCGGC CATGATGTAG ACGTTATGTG AGTTATAGTT GTACTCCATC TGTGGCCAAG      60
AATGTTGCCG TCCTCCTTGA AGT                                             83
```

(2) INFORMATION FOR SEQ ID NO:9:

(i) SEQUENCE CHARACTERISTICS:
(A) LENGTH: 84 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

```
CATCATGGCC GACAAGCCAA AGAACGGCAT CAAGGTTAAC TTCAAGATCC GCCACAACAT      60
TAAGGACGGC AGCGTTCAGC TCGC                                            84
```

(2) INFORMATION FOR SEQ ID NO:10:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

```
CGCCGATCGG AGTGTTCTGC TGATAATGGT CGGCGAGCTG AACGCTGCCG                 50
```

(2) INFORMATION FOR SEQ ID NO:11:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

```
AAGACTCGAG CCGAGGTCAA G                                               21
```

(2) INFORMATION FOR SEQ ID NO:12:

(i) SEQUENCE CHARACTERISTICS:

(A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

TCAAGCTTTA TGTCCAAGGG CGAGGAGCTC TTCACTGGAG TTGTC 45

(2) INFORMATION FOR SEQ ID NO:13:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GATGCTCGAG TCTTGTAGTT CCCGTCATCT TTGTAAAA 38

(2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GATGCGATCG GCGATGGCCC TGTCCTTTTA CCAGACAA 38

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TGAGAATTCG GATCCTTATT TGTATAGTTC ATCCATGCC 39

(2) INFORMATION FOR SEQ ID NO:16:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

TCCATTTAAA TATGAGCAAG GGCGAGGAGC TCTTCACTGG AGTTGTC 47

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (  i i  ) MOLECULE TYPE: cDNA (  x i  ) SEQUENCE DESCRIPTION: SEQ ID NO:17:

TTCCTTAATT AATTATTTGT ATAGTTCATC CATGCC                                      36

( 2 ) INFORMATION FOR SEQ ID NO:18:

(  i  ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (  i i  ) MOLECULE TYPE: cDNA (  x i  ) SEQUENCE DESCRIPTION: SEQ ID NO:18:

TGGAATAAGC TTTATGAGTA AAGGAGAAGA ACTTTT                                      36

( 2 ) INFORMATION FOR SEQ ID NO:19:

(  i  ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (  i i  ) MOLECULE TYPE: cDNA (  x i  ) SEQUENCE DESCRIPTION: SEQ ID NO:19:

AAGAATTCGG ATCCCTTTAG TGTCAATTGG AAGTCT                                      36

( 2 ) INFORMATION FOR SEQ ID NO:20:

(  i  ) SEQUENCE CHARACTERISTICS:
        ( A ) LENGTH: 751 base pairs
        ( B ) TYPE: nucleic acid
        ( C ) STRANDEDNESS: single
        ( D ) TOPOLOGY: linear (  i i  ) MOLECULE TYPE: cDNA (  x i  ) SEQUENCE DESCRIPTION: SEQ ID NO:20:

ATGAGTAAAG GAGAAGAACT TTTCACTGGA GTTGTCCCAA TTCTTGTTGA ATTAGATGGC            60
GATGTTAATG GGCAAAAATT CTCTGTTAGT GGAGAGGGTG AAGGTGATGC AACATACGGA            120
AAACTTACCC TTAAATTTAT TTGCACTACT GGGAAGCTAC CTGTTCCATG TCCAACGCTT            180
GTCACTACTT TCTCTTATGG TGTTCAATGC TTTTCTAGAT ACCCAGATCA TATGAAACAG            240
CATGACTTTT TCAAGAGTGC CATGCCCGAA GGTTATGTAC AGGAAAGAAC TATATTTTAC            300
AAAGATGACG GGAACTACAA GACACGTGCT GAAGTCAAGT TTGAAGGTGA TACCCTTGTT            360
AATAGAATCG AGTTAAAAGG TATTGATTTT AAAGAAGATG GAAACATTCT TGGACACAAA            420
ATGGAATACA ACTATAACTC ACATAATGTA TACATCATGG CAGACAAACC AAAGAATGGC            480
ATCAAAGTTA ACTTCAAAAT TAGACACAAC ATTAAAGATG GAAGCGTTCA ATTAGCAGAC            540
CATTATCAAC AAAATACTCC AATTGGCGAT GGCCCTGTCC TTTTACCAGA CAACCATTAC            600
CTGTCCACGC AATCTGCCCT TTCCAAAGAT CCCAACGAAA AGAGAGATCA CATGATCCTT            660
CTTGAGTTTG TAACAGCTGC TGGGATTACA CATGGCATGG ATGAACTATA CAAATAAATG            720
TCCAGACTTC CAATTGACAC TAAAGGGATC C                                           751

( 2 ) INFORMATION FOR SEQ ID NO:21:

(  i  ) SEQUENCE CHARACTERISTICS:
        ( A ) LENGTH: 14 base pairs (B) TYPE: nucleic acid
        (C) STRANDEDNESS: single
        (D) TOPOLOGY: linear (xi) SEQUENCE DESCRIPTION: SEQ ID NO:21:

AGGAAAGCTT TATG                                                                                                        1 4

MODIFICATION OF CRYPTIC SPLICE SITES IN HETEROLOGOUS GENES EXPRESSED IN FUNGI

BACKGROUND OF THE INVENTION

1. Field of the Invention

The present invention relates to a method for obtaining a recombinant fungal host cell comprising a nucleic acid sequence encoding a heterologous protein, wherein at least one cryptic splice site is modified in the nucleic acid sequence. The present invention also relates to an isolated nucleic acid sequence(s) with the modified cryptic splice site(s) as well as nucleic acid constructs, vectors, and recombinant host cells comprising said nucleic acid sequence(s). The present invention further relates to methods for the recombinant production of a polypeptide encoded by said nucleic acid sequence.

2. Description of the Related Art

Eukaryotic genes may be interrupted by intervening sequences (introns) which must be modified in precursor transcripts in order to produce functional mRNAs. This process of intron removal is known as pre-mRNA splicing. Usually, a branchpoint sequence of an intron is necessary for intron splicing through the formation of a lariat. Signals for splicing reside directly at the boundaries of the intron splice sites. The boundaries of intron splice sites usually have the consensus intron sequences GT and AG at their 5' and 3' extremities, respectively. While no 3' splice sites other than AG have been reported, there are reports of a few exceptions to the 5' GT splice site. For example, there are precedents where CT or GC is substituted for GT at the 5' boundary. There is also a strong preference for the nucleotide bases ANGT to follow GT where N is A, C, G, or T (primarily A or T in Saccharomyces species), but there is no marked preference for any particular nucleotides to precede the GT splice site. The 3' splice site AG is primarily preceded by a pyrimidine nucleotide base (Py), i.e., C or T.

The number of introns that can interrupt a fungal gene ranges from one to twelve or more introns (Rymond and Rosbash, 1992, In, E. W. Jones, J. R. Pringle, and J. R. Broach, editors, *The Molecular and Cellular Biology of the Yeast Saccharomyces*, pages 143–192, Cold Spring Harbor Laboratory Press, Plainview, N.Y.; Gurr et al., 1987, In Kinghorn, J. R. (ed.), *Gene Structure in Eukaryotic Microbes*, pages 93–139, IRL Press, Oxford). They may be distributed throughout a gene or situated towards the 5' or 3' end of a gene. In *Saccharomyces cerevisiae*, introns are located primarily at the 5' end of the gene. Introns may be generally less than 1 kb in size, and usually are less than 400 bp in size in yeast and less than 100 bp in filamentous fungi.

The *Saccharomyces cerevisiae* intron branchpoint sequence 5'-TACTAAC-3' rarely appears exactly in filamentous fungal introns (Gurr et al., 1987, supra). Sequence stretches closely or loosely resembling TACTAAC are seen at equivalent points in filamentous fungal introns with a general consensus NRCTRAC where N is A, C, G, or T, and R is A or G. For example, the fourth position T is invariant in both the *Neurospora crassa* and *Aspergillus nidulans* putative consensus sequences. Furthermore, nucleotides G, A, and C predominate in over 80% of the positions 3, 6, and 7, respectively, although position 7 in *Aspergillus nidulans* is more flexible with only 65% C. However, positions 1, 2, 5, and 8 are much less strict in both *Neurospora crassa* and *Aspergillus nidulans*. Other filamentous fungi have similar branchpoint stretches at equivalent positions in their introns, but the sampling is too small to discern any definite trends.

The heterologous expression of a gene encoding a polypeptide in a fungal host strain may result in the host strain incorrectly recognizing a region within the coding sequence of the gene as an intervening sequence or intron. For example, it has been found that intron-containing genes of filamentous fungi are incorrectly spliced in *Saccharomyces cerevisiae* (Gurr et al., 1987, In Kinghorn, J. R. (ed.), *Gene Structure in Eukaryotic Microbes*, pages 93–139, IRL Press, Oxford). Since the region is not recognized as an intron by the parent strain from which the gene was obtained, the intron is called a cryptic intron. This improper recognition may lead to aberrant splicing of the precursor mRNA molecules resulting in no production of biologically active polypeptide or in the production of several populations of polypeptide products with varying biological activity.

It is an object of the present invention to provide methods for removing cryptic splice sites within the coding sequences of genes to prevent improper splicing of precursor mRNA for heterologous expression by fungal host cells.

SUMMARY OF THE INVENTION

The present invention relates to methods for obtaining a recombinant fungal host cell, comprising introducing into a fungal host cell a nucleic acid sequence encoding a heterologous polypeptide, wherein at least one cryptic splice site is modified in the nucleic acid sequence. In one embodiment, the cryptic splice site(s) is modified by replacing at least one cryptic consensus sequence with a non-consensus sequence. In another embodiment, the cryptic splice site(s) is modified by replacing a first region comprising at least one cryptic intron or portion thereof with a second region which has a percent G+C content in the range of about 40% to about 70%. In another preferred embodiment, the cryptic splice site(s) is modified by replacing the cryptic consensus sequence(s) with a non-consensus sequence and by replacing a first region comprising a cryptic intron(s) or portion thereof with a second region which has a percent G+C content in the range of about 40% to about 70%.

The present invention also relates to nucleic acid sequences with at least one modified cryptic splice site, as well as nucleic acid constructs, vectors, and host cells comprising said nucleic acid sequences. The present invention further relates to methods for recombinant production of polypeptides encoded by said nucleic acid sequences.

DEFINITIONS

"Intron" is defined herein as an untranslated intervening nucleic acid sequence that interrupts the coding sequence of a gene and is excised from the primary mRNA transcript "Exon" is defined herein as segments of a gene transcribed and translated into a polypeptide.

"Primary mRNA transcript" is defined herein as the precursor mRNA product of a gene produced by transcription.

"RNA splicing" is defined herein as the excision of a transcribed intron sequence(s) from a primary mRNA transcript followed by the joining of the remaining exons to produce the mRNA product.

"Cryptic intron" is defined herein as a region of a coding sequence that is incorrectly recognized as an intron which is excised from the primary mRNA transcript A cryptic intron preferably has 10 to 1500 nucleotides, more preferably 20 to 1000 nucleotides, even more preferably 30 to 300 nucleotides, and most preferably 30 to 100 nucleotides.

"Consensus sequence" is defined herein as a nucleic acid sequence generally found at the 5' or 3' exon-intron boundary which contains the intron splice site.

"Cryptic splice site" is defined herein as the site at either the 5' or 3' boundary of a cryptic intron where aberrant splicing occurs.

"Cryptic consensus sequence" is defined herein as a nucleic acid sequence generally found at either the 5' or 3' boundary of a cryptic intron which contains the cryptic splice site. A cryptic consensus sequence preferably has no more than 10, more preferably no more than 6, even more preferably 3, and most preferably 2 nucleotides.

"Aberrant splicing" is defined herein as the improper excision of a region of a transcribed sequence from a primary mRNA transcript, wherein the region is incorrectly recognized as an intervening nucleic acid sequence.

"Amino acid wobble position" is defined herein as a nucleotide residue which, due to the degeneracy of the genetic code of the fungal host cell, can be replaced by another nucleotide.

"Recombinant fungal host cell" is defined herein as a fungal host cell comprising a heterologous nucleic acid sequence.

BRIEF DESCRIPTION OF THE FIGURES

FIG. 3 shows the GFP cDNA sequence (SEQ ID NO:20) with cryptic intron regions labeled as fragments A-D.

DETAILED DESCRIPTION OF THE INVENTION

Figure 1:
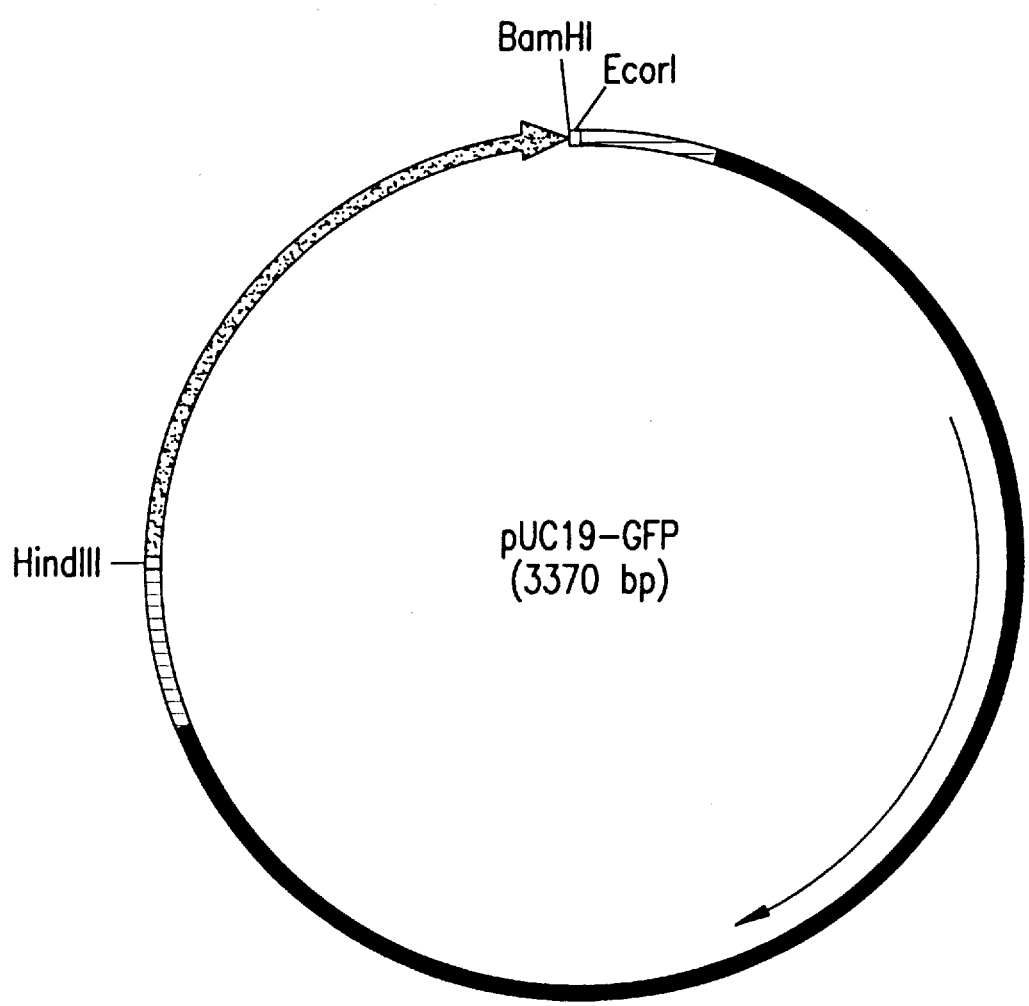
FIG. 1 shows a restriction map of pUC19-GFP.

The present invention relates to methods for obtaining a recombinant fungal host cell, comprising introducing into a fungal host cell a nucleic acid sequence encoding a heterologous polypeptide, wherein at least one cryptic splice site is modified in the nucleic acid sequence. The nucleic acid sequence may be a genomic sequence as well as the corresponding cDNA and RNA sequences. The nucleic acid sequence is preferably a cDNA sequence.

The cryptic splice site(s) may be identified by comparison of the heterologous mRNA, or cDNA synthesized from said mRNA, encoding the heterologous polypeptide produced in the recombinant fungal host cell with the mRNA, or cDNA sysnthesized from said mRNA, obtained from the parent cell. The parent cell is the source of the heterologous mRNA. Alternatively, the cryptic splice site(s) may be identified from the amino acid sequence of the polypeptide encoded heterologously by the nucleic acid sequence in the fungal host cell by comparison with the nucleic acid sequence of the parent cell and its deduced amino acid sequence. Cryptic splice sites may also be identified using knowledge of the boundaries or consensus intron sequences of authentic fungal intron splice sites (Rymond and Rosbash, 1992, supra; Gurr et al., 1987, supra).

The cryptic splice site(s) may be modified by replacing the cryptic consensus sequence(s) with a non-consensus sequence and/or replacing a first region of a cryptic intron(s) or portion thereof with a second region which has a percent G+C content in the range of about 40% to about 70%, preferably about 40% to about 60%, and more preferably about 40% to about 50%.

The 5' and 3' cryptic consensus sequences may be replaced with a non-consensus sequence by methods well known in the art including, but not limited to, oligonucleotide-directed mutagenesis, homologous recombination, site-specific mutagenesis, PCR mutagenesis, and chemical synthesis. In a preferred embodiment, the 5' cryptic consensus sequence is GT, GC, or CT and the 3' cryptic consensus sequence is AG. In a more preferred embodiment, the 5' cryptic consensus sequence is GTANGT, GCANGT, or CTANGT wherein N is A, C, G, or T. In another more preferred embodiment, the 3' cryptic consensus sequence is CAG, TAG, or AAG. Where there is more than one synthetic fragment, the fragments may be annealed together into one fragment using procedures known in the art. The entire coding sequence may then be reconstructed by amplifying the remaining 5' and 3' portions of the nucleic acid sequence surrounding the synthesized fragment with oligonucleotide primers specific for the gene.

The choice of nucleotides to replace the nucleotides of the cryptic consensus sequences is preferably based on a codon usage table such as Table I shown on the next page for Aspergillus the fungal host cell. The cryptic consensus sequence is preferably replaced by a nonconsensus sequence wherein nucleotides corresponding to amino acid wobble positions have been replaced with different nucleotides to yield the same amino acids.

TABLE I

| | | | |
|---|---|---|---|
| GCT | Ala | TTG | Leu |
| GCC | Ala | CTT | Leu |
| GCA | Ala | CTC | Leu |
| GCG | Ala | CTA | Leu |
| | | CTG | Leu |
| CGT | Arg | | |
| CGC | Arg | AAA | Lys |
| CGA | Arg | AAG | Lys |
| CGG | Arg | | |
| AGA | Arg | ATG | MET |
| AGG | Arg | | |
| | | TTT | Phe |
| AAT | Asn | TTC | Phe |
| AAC | Asn | | |
| | | CCT | Pro |
| GAT | Asp | CCC | Pro |
| GAC | Asp | CCA | Pro |
| | | CCG | Pro |
| TGT | Cys | | |
| TGC | Cys | TCT | Ser |
| | | TCC | Ser |
| CAA | Gln | TCA | Ser |
| CAG | Gln | TCG | Ser |
| | | AGT | Ser |
| GAA | Glu | AGC | Ser |
| GAG | Glu | | |
| | | ACT | Thr |
| GGT | Gly | ACC | Thr |
| GGC | Gly | ACA | Thr |

TABLE I-continued

| | | | |
|---|---|---|---|
| GGA | Gly | ACG | Thr |
| GGG | Gly | | |
| | | TGG | Trp |
| CAT | His | | |
| CAC | His | TAT | Tyr |
| | | TAC | Tyr |
| ATT | Ile | | |
| ATC | Ile | GTT | Val |
| ATA | Ile | GTC | Val |
| | | GTA | Val |
| TTA | Leu | GTG | Val |

Procedures for replacing a first region of a cryptic intron or portion thereof with a second region may be accomplished using the same procedures described above for replacing a cryptic consensus sequence with a nonconsensus sequence. In one embodiment, the second region has the same number of nucleotides as the first region. In a preferred embodiment, the first and second regions preferably have 10 to 500 nucleotides, more preferably 10 to 200 nucleotides, and most preferably 10 to 100 nucleotides flanking the 5' and/or 3' boundaries of the cryptic intron. In a cryptic intron, a branchpoint sequence may or may not be present. In a preferred embodiment, the cryptic intron sequence comprises a branchpoint sequence of at least seven nucleotides a-b-c-d-e-f-g wherein a is A, C, G, or T; b is A or G; c is C, d is T; e is A or T; f is A; and g is C. In a more preferred embodiment, the branchpoint sequence contains at least seven nucleotides a-b-c-d-e-f-g wherein a is A, C, G, or T; b is A; c is C, d is T; e is A; f is A; and g is C.

In a preferred embodiment, the amino acid sequence of the heterologous polypeptide produced by the fungal host cell is identical to the amino acid sequence of the wild-type polypeptide. In another preferred embodiment, the number of amino acid residues in the heterologous polypeptide produced by the fungal host cell is the same as the number of amino acid residues in the wild-type polypeptide. In another preferred embodiment, the non-consensus sequence(s) have the same number of nucleotides as the cryptic consensus sequence(s).

The amino acid sequence of the heterologous polypeptide produced by the recombinant fungal host cell may differ from the amino acid sequence of the wild-type polypeptide by an insertion or deletion of one or more amino acid residues and/or the substitution of one or more amino acid residues by different amino acid residues. Preferably, amino acid changes are of a minor nature, that is conservative amino acid substitutions that do not significantly affect the folding or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification, such as a poly-histidine tract, an antigenic epitope or a binding domain. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalaine, tryptophan, tyrosine) and small amino acids (such as glycine, alanine, serine, threonine, methionine).

The term "heterologous polypeptide" is not meant herein to refer to a specific length of the encoded product and, therefore, encompasses peptides, oligopeptides, and proteins. Furthermore, the term "heterologous polypeptide" may encompass two or more polypeptides combined to form the product. The heterologous polypeptides may be obtained from prokaryotic sources (e.g., hydrolases from Bacillus species, i.e., alpha-amylases, proteases, lipases, etc.), eukaryotic sources (e.g., human insulin, human growth hormone, bovine chymosin, Factor VIII, green fluorescent protein, etc.), and fungal sources other than the fungal host (e.g., Myceliophthora laccases, Polyporus laccases, Coprinus peroxidases, Humicola lipases, Aspergillus amylases, etc.). Heterologous polypeptides also may include hybrid polypeptides which comprise a combination of partial or complete polypeptide sequences obtained from at least two different polypeptides wherein at least one is heterologous to the fungal host (e.g., a nucleic acid sequence encoding a Myceliophthora laccase fused to a nucleic acid sequence encoding the Aspergillus niger glucoamylase signal peptide and propeptide). Heterologous polypeptides further may include naturally occurring allelic and engineered variations of the above mentioned polypeptides.

Preferably, the heterologous polypeptide is a hormone, an enzyme, a receptor, or a reporter. In a more preferred embodiment, the heterologous polypeptide is an oxidoreductase, a transferase, a hydrolase, a lyase, an isomerase, or a ligase. In an even more preferred embodiment, the heterologous polypeptide is an amninopeptidase, an amylase, a carbohydrase, a carboxypeptidase, a catalase, a cellulase, a chitinase, a cutinase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, a mutanase, an oxidase, a pectinolytic enzyme, a peroxidase, a phytase, a polyphenoloxidase, a proteolytic enzyme, a ribonuclease, or a xylanase.

In another even more preferred embodiment, the heterologous polypeptide is an Aequorea victoria green fluorescent protein (GFP). GFP possesses a number of desirable traits as a universal reporter to visualize gene expression and protein localization in vivo in a wide spectrum of organisms including Escherichia coli, yeast, plant cells, worm, fly, and mammals (Chalfie et al., 1994, Science 263:802–805; Delagrave et al., 1995, BioTechnology 13:151–154; Heim et al., 1995, Nature 373:663–664; Sheen et al., 1995, Plant Journal 8:777–784; Prasher, 1995, TIG 8:320–323; Haseloff and Amos, 1995, TIG 8:328–329). The use of GFP as a reporter for gene expression in filamentous fungi has not been reported.

The present invention also relates to isolated nucleic acid sequence(s) with a modified cryptic splice site(s) produced by the methods of the present invention. The nucleic acid sequence(s) with a modified cryptic splice site(s) further encompasses both the genomic sequence as well as the corresponding cDNA and RNA sequences, and the phrase "nucleic acid sequences" as used herein will be understood to encompass all such variations including synthetic DNA.

The present invention also relates to nucleic acid constructs comprising said nucleic acid sequence(s). "Nucleic acid construct" shall generally be understood to mean a nucleic acid molecule, either single- or double-stranded, which is isolated from a naturally occurring gene or which has been modified to contain segments of nucleic acid which are combined and juxtaposed in a manner which would not otherwise exist in nature. In a nucleic acid construct of the present invention, the nucleic acid sequence may be of genomic, cDNA, semisynthetic, or synthetic origin.

The present invention also relates to recombinant expression vectors comprising the nucleic acid construct of the present invention. The recombinant expression vector may be any vector which can be conveniently subjected to recombinant DNA procedures and can bring about the expression of the nucleic acid sequence with at least one modified cryptic splice site. The choice of a vector will typically depend on the compatibility of the vector with the fungal host cell into which the vector is to be introduced. The vector may be a linear or a closed circular plasmid. The vector system may be a single vector or plasmid or two or more vectors or plasmids which together contain the total DNA to be introduced into the genome of the fungal host.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the fungal cell, is integrated into the genome and replicated together with the chromosome(s) into which it has been integrated. For integration, the vector may rely on the nucleic acid sequence with at least one modified cryptic splice site or any other element of the vector for stable integration of the vector into the genome by homologous or nonhomologous recombination. Alternatively, the vector may contain additional nucleic acid sequences for directing integration by homologous recombination into the genome of the fungal host. The additional nucleic acid sequences enable the vector to be integrated into the host cell genome at a precise location(s) in the chromosome(s). To increase the likelihood of integration at a precise location, there should be preferably two nucleic acid sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleic acid sequences may be any sequence that is homologous with a target sequence in the genome of the fungal host cell, and, furthermore, may be non-encoding or encoding sequences.

For autonomous replication, the vector may further comprise an origin of replication enabling the vector to replicate autonomously in the host cell in question. Examples of origin of replications for use in a yeast host cell are the 2 micron origin of replication and the combination of CEN3 and ARS 1. Any origin of replication may be used which is compatible with the fungal host cell of choice.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. The selectable marker may be selected from the group including, but not limited to, amdS (acetamidase), argB (ornithine carbamoyltransferase), bar (phosphinothricin acetyltransferase), hygB (hygromycin phosphotransferase), niaD (nitrate reductase),pyrG (orotidine-5'-phosphate decarboxylase), and sC (sulfate adenyltransferase), and trpC (anthranilate synthase). Preferred for use in an Aspergillus cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243 where the selectable marker is on a separate vector.

In the vector, the nucleic acid sequence comprising at least one modified splice site is operably linked to control sequences which are required for the expression of the coding sequence of the nucleic acid sequence to which they are ligated. The term "control sequences" is meant herein to include all components whose presence is necessary or advantageous for expression of the coding sequence of the nucleic acid sequence. The control sequences may be native to the nucleic acid sequence encoding the heterologous polypeptide or may be obtained from foreign sources. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. For expression under the direction of control sequences, a gene to be used according to the present invention is operably linked to the control sequences in such a way that expression of the coding sequence is achieved under conditions compatible with the control sequences. The term "coding sequence" as defined herein is a sequence which is transcribed into mRNA and translated into a heterologous polypeptide when placed under the control of the above mentioned control sequences. The boundaries of the coding sequence are determined by a translation start codon at the 5'-termiinus and a translation stop codon at the 3'-terminus. A coding sequence can include, but is not limited to, DNA, cDNA, and recombinant nucleic acid sequences.

As noted above, the nucleic acid sequence of the present invention may be operably linked to a suitable promoter sequence. The promoter sequence is a nucleic acid sequence which is recognized by the fungal host cell for expression of the nucleic acid sequence. The promoter sequence contains transcription and translation control sequences which mediate the expression of the heterologous polypeptide. The promoter may be any nucleic acid sequence which shows transcriptional activity in the fungal host cell of choice and may be obtained from genes encoding polypeptides either homologous or heterologous to the host cell. Examples of suitable promoters for directing the transcription of a nucleic acid construct of the invention in a filamentous fungal host are promoters obtained from the genes encoding *Aspergillus oryzae* TAKA amylase, *Rhizomucor miehei* aspartic proteinase, *Aspergillus niger* neutral α-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and hybrids thereof. In a yeast host, a useful promoter is the *Saccharomyces cerevisiae* enolase (eno-1) promoter. Particularly preferred promoters are the TAKA amylase, NA2-tpi (a hybrid of the promoters from the genes encoding *Aspergillus niger* neutral α-amylase and *Aspergillus oryzae* triose phosphate isomerase), and glaA promoters.

The nucleic acid sequence of the present invention may also be operably linked to a terminator sequence at its 3' terminus. The terminator sequence may be native to the nucleic acid sequence encoding the heterologous polypeptide or may be obtained from foreign sources. Any terminator which is functional in the fungal host cell of choice may be used in the present invention, but particularly preferred terminators are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Saccharomyces cerevisiae* enolase.

The nucleic acid sequence of the present invention may also be operably linked to a suitable leader sequence. A leader sequence is a nontranslated region of a mRNA which is important for translation by the fungal host. The leader sequence is operably linked to the 5' terminus of the nucleic acid sequence encoding the heterologous polypeptide. The leader sequence may be native to the nucleic acid sequence encoding the heterologous polypeptide or may be obtained from foreign sources. Any leader sequence which is functional in the fungal host cell of choice may be used in the present invention, but particularly preferred leaders are obtained from the genes encoding *Aspergillus oryzae* TAKA amylase and *Aspergillus oryzae* triose phosphate isomerase.

A polyadenylation sequence may also be operably linked to the 3' terminus of the nucleic acid sequence of the present invention. The polyadenylation sequence is a sequence which when transcribed is recognized by the fungal host to add polyadenosine residues to transcribed mRNA. The polyadenylation sequence may be native to the nucleic acid sequence encoding the heterologous polypeptide or may be obtained from foreign sources. Any polyadenylation sequence which is functional in the fungal host of choice may be used in the present invention, but particularly preferred polyadenylation sequences are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

To avoid the necessity of disrupting the cell to obtain the heterologously expressed polypeptide, and to minimize the amount of possible degradation of the expressed polypeptide within the cell, it is preferred that expression of the polypeptide gene gives rise to a product secreted outside the cell. To this end, the heterologous polypeptide of the present invention may be linked to a signal peptide linked to the amino terminus of the polypeptide. A signal peptide is an amino acid sequence which permits the secretion of the heterologous polypeptide from the fungal host into the culture medium. The signal peptide may be native to the heterologous polypeptide of the invention or may be obtained from foreign sources. The 5' end of the coding sequence of the nucleic acid sequence of the present invention may inherently contain a signal peptide coding region naturally linked in translation reading frame with the segment of the coding region which encodes the secreted heterologous polypeptide. Alternatively, the 5' end of the coding sequence may contain a signal peptide coding region which is foreign to that portion of the coding sequence which encodes the secreted heterologous polypeptide. The foreign signal peptide may be required where the coding sequence does not normally contain a signal peptide coding region. Alternatively, the foreign signal peptide may simply replace the natural signal peptide to obtain enhanced secretion of the desired heterologous polypeptide. The foreign signal peptide coding region may be obtained from a glucoamylase or an amylase gene from an Aspergillus species, a lipase or proteinase gene from *Rhizomucor miehei*, the gene for the α-factor from *Saccharomyces cerevisiae*, or the calf prepro-chymosin gene. An effective signal peptide for fungal host cells is the *Aspergillus oryzae* TAKA amylase signal, Aspergillus niger neutral amylase signal, the Rhizomucor miehei aspartic proteinase signal, the *Humicola lanuginosus* cellulase signal, or the *Rhizomucor miehei* lipase signal. However, any signal peptide capable of permitting secretion of the heterologous polypeptide in a fungal host of choice may be used in the present invention.

The nucleic acid sequence of the present invention may also be linked to a propeptide coding region. A propeptide is an amino acid sequence found at the amino terminus of apropolypeptide or proenzyme. Cleavage of the propeptide from the propolypeptide yields a mature biochemically active polypeptide. The resulting polypeptide is known as a propolypeptide or proenzyme (or a zymogen in some cases). Propolypeptides are generally inactive and can be converted to mature active polypeptides by catalytic or autocatalytic cleavage of the propeptide from the propolypeptide or proenzyme. The propeptide coding region may be native to the heterologous polypeptide or may be obtained from foreign sources. The foreign propeptide coding region may be obtained from the *Saccharomyces cerevisiae* alpha-factor gene or *Myceliophthora thermophila* laccase gene (WO 95/33836).

The procedures used to ligate the elements described above to construct the recombinant expression vector of the present invention are well known to one skilled in the art (see, for example, Sambrook et al., *Molecular Cloning, A Laboratory Manual*, 2nd ed., Cold Spring Harbor, N.Y., 1989).

The present invention also relates to recombinant fungal host cells produced by the methods of the present invention which are advantageously used with the recombinant vector of the present invention. The cell is preferably transformed with a vector comprising a nucleic acid sequence of the invention followed by integration of the vector into the host chromosome. "Transformation" means introducing a vector comprising a nucleic acid sequence with at least one modified cryptic splice sites into a fungal host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of fungal host cells will to a large extent depend upon the gene encoding the heterologous polypeptide and its source. The fungal host cell may be a yeast cell or a filamentous fungal cell.

"Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (for example, genus Schizosaccharomyces), Nadsonioideae, Lipomycoideae, and Saccharomycoideae (for example, genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (for example, genera Sorobolomyces and Bullera) and Cryptococcaceae (for example, genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, for example, *Biochemistry and Genetics of Yeast*, Bacil, M., Horecker, B. J., and Stopani, A. O. M., editors, 2nd edition, 1987; *The Yeasts*, Rose, A. H., and Harrison, J. S., editors, 2nd edition, 1987; and *The Molecular Biology of the Yeast Saccharomyces*, Strathern et al, editors, 1981).

"Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, for example, Neurospora, Eupenicillium (=Penicillium), Emericella (=Aspergillus), Eurotiun (=Aspergillus), and the true yeasts listed above. Examples of Basidiomycota include mushrooms, rusts, and smuts. Representative groups of Chytridiomycota include, for example, Allomyces, Blastocladiella, Coelomomyces, and aquatic fungi. Representative groups of Oomycota include, for example, Saprolegniomycetous aquatic fungi (water molds) such as Achlya. Examples of mitosporic fungi include Aspergillus, Penicilliun, Candida, and Alternaria. Representative groups of Zygomycota include, for example, Rhizopus and Mucor.

"Filamentous fungi" include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In one embodiment, the fungal host cell is a yeast cell. In a preferred embodiment, the yeast host cell is a cell of the species of Candida, Kluyveromyces, Saccharomyces, Schizosaccharomyces, Pichia, and Yarrowia. In a most preferred embodiment, the yeast host cell is a *Saccharomyces cerevisiae* cell, a Saccharomyces carlsbergensis, *Saccharomyces diastaticus* cell, a *Saccharomyces douglasii* cell, a *Saccharomyces kluyveri* cell, a *Saccharomyces norbensis* cell, or a *Saccharomyces oviformis* cell. In another preferred embodiment, the yeast host cell is a *Kluyveromyces lactis* cell. In another most preferred embodiment, the yeast host cell is a *Yarrowia lipolytica* cell.

In another embodiment, the fungal host cell is a filamentous fungal cell. In a preferred embodiment, the filamentous fungal host cell is a cell of the species of, but not limited to, Acremonium, Aspergillus, Fusarium, Humicola, Myceliophthora, Mucor, Neurospora, Penicillium, Thielavia, Tolypocladium, and Trichoderma. In a more preferred embodiment, the filamentous fungal host cell is an Aspergillus cell. In another more preferred embodiment, the filamentous fungal host cell is an Acremonium cell. In another more preferred embodiment, the filamentous fungal host cell is a Fusarium cell. In another more preferred embodiment, the filamentous fungal host cell is a Humicola cell. In anothermore preferred embodiment, the filamentous fungal host cell is a Myceliophthora cell. In another even more preferred embodiment, the filamentous fungal host cell is a Mucor cell. In another more preferred embodiment, the filamentous fungal host cell is a Neurospora cell In another more preferred embodiment, the filamentous fungal host cell is a Penicillium cell. In another more preferred embodiment, the filamentous fungal host cell is a Thielavia cell. In another more preferred embodiment, the filamentous fungal host cell is a Tolypocladiun cell. In another more preferred embodiment, the filamentous fungal host cell is a Trichoderma celL In a most preferred embodiment, the filamentous fungal host cell is an *Aspergillus oryzae* cell, an *Aspergillus niger* cell, an *Aspergillus foetidus* cell, or an *Aspergillus japonicus* cell. In another most preferred embodiment, the filamentous fungal host cell is a *Fusarium oxysporum* cell or a *Fusarium graminearum* cell. In another most preferred embodiment, the filamentous fungal host cell is a *Humicola insolens* cell or a *Humicola lanuginosus* cell. In another most preferred embodiment, the filamentous fungal host cell is a *Myceliophthora thermophila* cell. In another most preferred embodiment, the filamentous fungal host cell is a *Mucor miehei* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma reesei* cell, a *Trichoderma viride* cell, a *Trichoderma longibrachiatum* cell, a *Trichoderma harzianum* cell, or a *Trichoderma koningii* cell.

The recombinant fungal host cells of the present invention may further comprise one or more sequences which encode one or more factors that are advantageous in the expression of the heterologous polypeptide, for example, an activator (e.g., a trans-acting factor), a chaperone, and a processing protease. The nucleic acids encoding one or more of these factors are preferably not operably linked to the nucleic acid encoding the heterologous polypeptide. An activator is a protein which activates transcription of a nucleic acid sequence encoding a polypeptide (Kudla et al., 1990, EMBO Journal 9:1355–1364; Jarai and Buxton, 1994, *Current Genetics* 26:2238–244; Verdier, 1990, *Yeast* 6:271–297). The nucleic acid sequence encoding an activator may be obtained from the genes encoding *Saccharomyces cerevisiae* heme activator protein 1 (hap1), *Saccharomyces cerevisiae* galactose metabolizing protein 4 (gal4), and *Aspergillus nidulans* ammonia regulation protein (areA). For further examples, see Verdier, 1990, supra and MacKenzie et al., 1993, *Journal of General Microbiology* 139:2295–2307. A chaperone is a protein which assists another polypeptide in folding properly (Hartl et al., 1994, *TIBS* 19:20–25; Bergeron et al., 1994, *TIBS* 19:124–128; Demolder et al., 1994, *Journal of Biotechnology* 32:179–189; Craig, 1993, *Science* 260:1902–1903; Gething and Sambrook, 1992, *Nature* 355:33–45; Puig and Gilbert, 1994, *Journal of Biological Chemistry* 269:7764–7771; Wang and Tsou, 1993, *The FASEB Journal* 7: 1515–11157; Robinson et al., 1994, *Bio/Technology* 1:381–384). The nucleic acid sequence encoding a chaperone may be obtained from the genes encoding *Aspergillus oryzae* protein disulphide isomerase, *Saccharomyces cerevisiae* calnexin, *Saccharomyces cerevisiae* BiP/GRP78, and *Saccharomyces cerevisiae* Hsp70. For further examples, see Gething and Sambrook, 1992, supra, and Hartl et al., 1994, supra. A processing protease is a protease that cleaves a propeptide to generate a mature biochemically active polypeptide (Enderlin and Ogrydziak, 1994, *Yeast* 10:67–79; Fuller et al., 1989, *Proceedings of the National Academy of Sciences USA* 86:1434–1438; Julius et al., 1984, *Cell* 37:1075–1089; Julius et al., 1983, *Cell* 32:839–852). The nucleic acid sequence encoding a processing protease may be obtained from the genes encoding *Aspergillus niger* Kex2, *Saccharomyces cerevisiae* dipeptidylaminopeptidase, *Saccharomyces cerevisiae* Kex2, and *Yarrowia lipolytica* dibasic processing endoprotease (xpr6). Any factor that is functional in the fungal host cell of choice may be used in the present invention.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, Proceedings of the National Academy of Sciences USA 81:1470–1474. A suitable method of transforming Fusarium species is described by Malardier et al., 1989, *Gene* 78:147–156 or in copending U.S. Ser. No. 08/269,449 now abandoned. Yeast may be transformed using the procedures described by Becker and Guarente, In Abelson, J. N. and Simon, M. I. (eds.), *Guide to Yeast Genetics and Molecular Biology*, Methods in Enzymology, Volume 194, pp 182–187, Academic Press, Inc., New York; Ito et al., 1983, *Journal of Bacteriology* 153:163; and Hinnen et al., 1978, *Proceedings of the National Academy of Sciences USA* 75:1920.

The present invention also relates to methods of producing the heterologous polypeptide comprising culturing the recombinant fungal host cells under conditions conducive for expression of the heterologous polypeptide. The fungal cells of the present invention are cultivated in a nutrient medium suitable for production of the heterologous polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the heterologous polypeptide to be expressed and/or isolated. The cultivation takes place in a suitable nutrient medium comprising carbon and nitrogen sources and inorganic salts, using procedures known in the art (see, e.g., Bennett, J. W. and LaSure, L., eds., *More Gene Manipulations in Fungi*, Academic Press, CA, 1991). Suitable media are available from commercial suppliers or may be prepared according to published compositions (e.g., in catalogues of the American Type Culture Collection). If the heterologous polypeptide is secreted into the nutrient medium, the polypeptide can be recovered directly from the medium. If the heterologous polypeptide is not secreted, it is recovered from cell lysates.

The expressed heterologous polypeptide may be detected using methods known in the art that are specific for the particular polypeptide. These detection methods may include the use of specific antibodies, formation of an enzyme product, or disappearance of an enzyme substrate. For example, if the heterologous polypeptide has enzymatic activity, an enzyme assay may be used. Alternatively, if polyclonal or monoclonal antibodies specific to the heterologous polypeptide are available, immunoassays may be employed using the antibodies to the polypeptide. The techniques of enzyme assay and immrunoassay are well known to those skilled in the art.

The resulting heterologous polypeptide may be recovered by methods known in the arts For example, the polypeptide may be recovered from the nutrient medium by conventional procedures including, but not limited to, centrifugation, filtration, extraction, spray-drying, evaporation, or precipitation. The recovered polypeptide may then be furter purified by a variety of chromatographic procedures, e.g., ion exchange chromatography, gel filtration chromatography, affinity chromatography, or the like.

The present invention is further described by the following examples which should not be construed as limiting the scope of the invention.

EXAMPLES

Example 1 Oligonucleotide Primers

The following oligonucleotide primers are synthesized with an Applied Biosystems Model 394 DNA/RNA Synthesizer (Applied Biosystems, Inc., Foster City, Calif.) according to the manufacturer's instructions:

95–88 TGTCACTACTTTCTCTTATGG (SEQ ID NO:1)
95–89 GTAATGGTTGTCTGGTAAAAG (SEQ ID NO:2)
95–448 TATCGGCCGCACCGGCCAAGATGAG-TAAAGGAGAAGAACTT (SEQ ID NO:3)
95–449 ATACATGCATTTATTTGTATAGTTCATC-CATGCCATGTGT (SEQ ID NO:4)
95–656 TGTTACAAACTCAAGAAGGAT (SEQ ID NO:5)
95–1202 ATGAGTAAAGGAGAAGAACTTTTC (SEQ ID NO:6)
95–1411 AAGACTCGAGCCGAGGTCAAGTTC-GAGGGCGATACCCTTTGTTAACCGC ATCGAGCT-CAAGGGCATTGACTTCAAGGAGGACGGC (SEQ ID NO:7)
95–1412 GCTTGTCGGCCATGATGTAGACGTTAT-GTGAGTTATAGTTGTACTCCATC TGTGGCCAA-GAATGTTGCCGTCCTCCTTGAAGT (SEQ ID NO:8)
951413 CATCATGGCCGACAAGCCAAAGAACG-GCATCAAGGTTAACTTCAAGATCCG CCACAA-CATTAAGGACGGCAGCGTTCAGCTCGC (SEQ ID NO:9)
95–1414 CGCCGATCGGAGTGTTCTGCTGATAATG-GTCGGCGAGCTGAACGCTGC CG (SEQ ID NO:10)
95–1415 AAGACTCGAGCCGAGGTCAAG (SEQ ID NO:11)
95–1422 TCAAGCTTTATGTCCAAGGGCGAG-GAGCTCTTCACTGGAGTTGTC (SEQ ID NO:12)
95–1457 GATGCTCGAGTCTTGTAGTTCCCGT-CATCTTTGTAAAA (SEQ ID NO:13)
95–1458 GATGCGATCGGCGATGGCCCTGTCCTTT-TACCAGACAA (SEQ ID NO:14)
95–1464 TGAGAATTCGGATCCTTATTTGTATAGT-TCATCCATGCC (SEQ ID NO:15)
96–67 TCCATTTAAATATGAGCAAGGGCGAG-GAGCTCTTCACTGGAGTTGTC (SEQ ID NO:16)
96–68 TTCCTTAATTAATTATTTGTATAGT-TCATCCATGCC (SEQ ID NO:17)
GFP2: TGGAATAAGCTTTATGAGTAAAGGAGAA-GAACTTTT (SEQ ID NO:18)
GFP1: AAGAATTCGGATCCCTTTAGTGTCAAT-TGGAAGTCT (SEQ ID NO:19)

Example 2 DNA Sequencing

Nucleotide sequences are determined with an Applied Biosystems Model 373A Automatic DNA Sequencer (Applied Biosystems, Inc., Foster City, Calif.) on both strands employing Taq polymerase cycle-sequencing with fluorescent labeled dideoxynucleotides (Giesecke et al., 1992, *Journal of Virol. Methods* 38:47–60) using the M13 reverse (–48) and M13 (–20) forward primers (New England Biolabs, Beverly, Mass.) and primers unique to the DNA being sequenced.

Example 3 Aequorea victoria Green Fluorescent Protein (GFP) Analysis

The production of GFP is determined using a Perkin-Elmer Cetus LS50B Fluorimeter (Perkin-Elmer Corp., Norwalk, Conn.). Specifically, 100 microliters of a protein extract are placed into a 96 well microtiter plate which is placed into the Perkin-Elmer Cetus LS50B plate reader. The extracts are exposed to light at 395 nm and the emission spectrum is read from 400 nm to 600 nm.

A Zeiss Axioplan microscope (Carl Zeiss, Inc., ThoRNwood, N.Y.) with a GFP filter set (Chroma Technology Corp., Brattleboro, Vt.) is used to view mycelia for GFP fluorescence.

Example 4 Construction of Expression Vector pShTh34

A filamentous fungal expression vector pShTh34 is constructed to place the GFP structural gene under the control of the TAKA amylase promoter, signal sequence and terminator.

Total RNA, isolated from *Aequoria Victoria* by standard procedures (Sambrook et al., 1989, supra), is converted into cDNA using the AMV reverse transcriptase (Promega, Madison, Wis.) as recommended by the manufacturer. The cDNA is then PCR amplified, using PCR primers designed on the basis of a previously published GFP sequence (Prasher et al., 1992, *Gene* 111:229–233; GenBank Accession No. M62653) together with the UITma™ polymerase (Perkin Elmer, Foster City, Calif.). The sequences of the primers are shown above as SEQU ID NOS:18 and 19.

Restriction endonuclease sites are inserted in the 5' (a HindIII site) and 3' (EcoRI and BamHI sites) primers to facilitate the cloning of the PCR amplified GFP cDNA into a slightly modified pUC19 vector. The details of the construction are LacZ Shine-Dalgarno AGGA, immediately followed by the 5' HindIII site plus an extra T and the GFP ATG codon, yielding the following DNA sequence at the LacZ promoter GFP fusion point: PLacZ-AGGAAAGCTTTATG-GFP (SEQ ID NO:21). At the 3' end of the GFP cDNA, the base pair corresponding to nucleotide 770 in the published GFP sequence is fused to the EcoRI site of the pUC19 multiple cloning site (MCS) through a PCR generated BamHI, EcoRI linker region as shown in FIG. 1.

Figure 2:
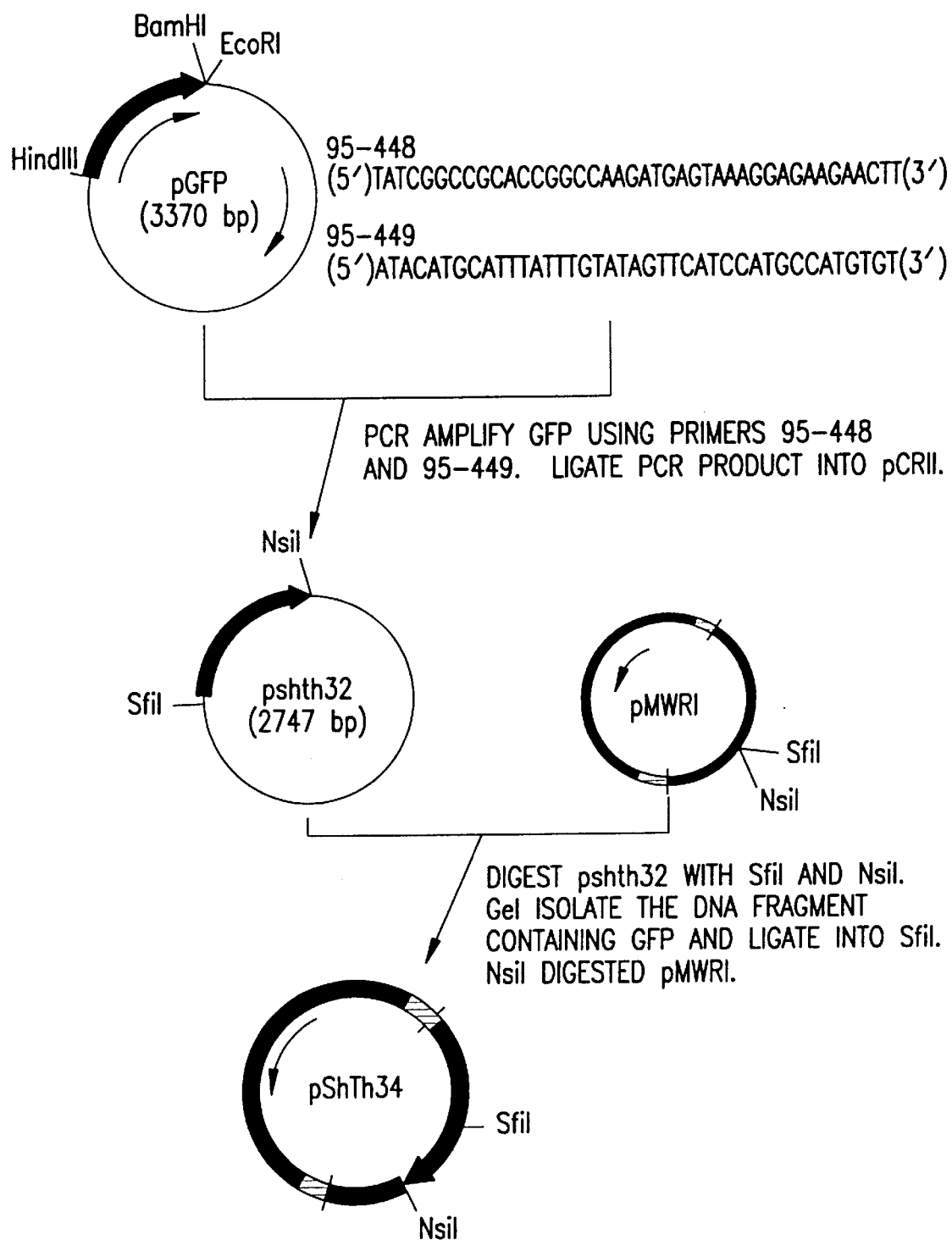
FIG. 2 shows the construction of pShTh34 which includes sequences 95–448 (SEQ ID NO:3) and 95–449 (SEQ ID NO:4).

The GFP structural gene is PCR amplified using pUC19-GFP as a template with oligonucleotide primers 95–448 and 95–449 described in Example 1. The amplification reaction contains the following components: 200 micromoles each of dATP, dCTP, dGTP, and dTTP, 50 ng template, 30 picomoles of each primer, 1x Taq polymerase buffer, and 0.5 units Taq polymerase (Stratagene Cloning Systems, La Jolla, Calif.). The reaction is incubated in an Ericomp Thermal Cycler programmed as follows: 1 cycle at 94° C. for 5 minutes; 30 cycles each at 94° C. for 1 minute, 60° C. for 1 minute, and 74° C. for 1 minute; and 1 cycle at 74° C. for 15 minutes. Use of these primers results in the addition of a SfiI restriction site immediately upstream of the ATG start codon and a NsiI site immediately downstream of the stop codon of GFP. The fragment is isolated using standard methods of agarose electrophoresis. The resulting fragment is subcloned into pMWR1 to produce pShTh34 as shown in FIG. 2.

Example 5 Filamentous Fungal Transformation of pShTh34 pShTh34 is co-transformed with pPyrG (Fungal Genetics Stock Center, Kansas City, Kans.) into *Aspergillus oryzae* HowB104pyrG protoplasts. The transformation is conducted with protoplasts at a concentration of 2×10$^7$ protoplasts per ml. One hundred μl of protoplasts are placed on ice with 10 μg DNA for 30 minutes. One ml of SPTC (40% PEG 4000, 0.8M sorbitol, 0.05M Tris pH 8.0, 0.05M CaCl$_2$) is added and the protoplasts are incubated at 34° C. for 20 minutes. The protoplasts are plated directly onto plates containing Minimal Medium (per liter: 6 g of NaNO$_3$, 0.52 g of KCl, 1.52 g of KH$_2$PO$_4$, 1 ml trace metals solution, 1 g of glucose, 500 mg of MgSO$_4$-7H$_2$O, 342.3 g of sucrose and 20 g of Noble agar at pH 6.5). The trace metals solution (1000X) is comprised of 22 g of ZnSO$_4$-7H$_2$O, 11 g of H$_3$BO$_3$, 5 g of MnCl$_2$-4H$_2$O, 5 g of FeSO$_4$-7H$_2$O, 1.6 g of CoCl$_2$-5H$_2$O, 1.6 g of (NH$_4$)$_6$Mo$_7$O$_{24}$, and 50 g of Na$_4$EDTA per liter. Plates are incubated 5–7 days at 37° C. Transformants are transferred to plates of the same medium without sucrose and incubated 3–5 days at 37° C. The transformants are purified by streaking spores and picking isolated colonies using the same plates under the same conditions. The resulting transformants are designated *Aspergillus oryzae* ShTh340.

Example 6 Extraction of GFP

The *Aspergillus oryzae* ShTh340 transformants described in Example 5 are screened for the presence of the GFP expression by fluorimetric analysis as described in Example 3. Ten *Aspergillus oryzae* ShTh340-19 transformants are grown in a 12 well microtiter plate for 1–5 days at 37° C. statically in 4 ml of MY51 medium comprising the following components per liter: 50 g of maltose, 2 g of MgSO$_4$-7H$_2$O, 10 g of KH$_2$PO$_4$, 2 g of K$_2$SO$_4$, 2 of citric acid, 10 g of yeast extract, 0.5 ml of trace metals solution as described in Example 5, 1 g of urea, and 2 g of (NH$_4$)$_2$SO4. The mycelial mat is harvested, transferred to 1.5 ml Eppendorf tubes, and placed on dry ice for 5 minutes. The Eppendorf tube is then placed into a Speed-Vac® (Savant Instruments, Inc., Farmingdale, N.Y.) and dried overnight at room temperature under vacuum. The dried culture is crushed in the tube using a sterile lancet. The powdered culture is resuspended in 400 microliters of 50 mM sodium phosphate—0.5M NaCl pH 5.5 containing 1 mM PMSF and 0.1 mM pepstatin. Mycelial debris is pelleted in a Sorvall Microcentrifuge Model MC12V (DuPont Instruments, Inc., Newtown, Conn.) at full speed for 20 minutes. A volume of 200 microliters of the supernatant is transferred to a new Eppendorf tube and assayed according to the procedure described in Example 3.

None of the *Aspergillus oryzae* ShTh340-19 transformants produces detectable fluorescence.

Example 7 mRNA Analysis

Total RNA is isolated from the *Aspergillus oryzae* ShTh340-19 transformant described in Example 6 by the procedure of Timberlake and Barnard (1981, *Cell* 26:29–37).

Specific GFP cDNA is synthesized using a 3' Race Kit (Bethesda Research Laboratories, Gaithersburg, Md.) according to the manufacturer's instructions. One microgram of total RNA from the transformant is used in the reaction with the 3' UAP oligonucleotide primer along with the specific 5' oligonucleotide primer 95–1202 described in Example 1. The amplification reaction contains the following components: 200 micromole each of dATP, dCTP, dGTP, and dTTP, 1 picomole of each primer, 50 ng template, 1× Taq polymerase buffer, and 0.5 units Taq polymerase. The reaction is incubated in an Ericomp Thermal Cycler programmed as follows: One cycle at 94° C. for 5 minutes; thirty cycles each at 94° C. for 1 minute, 50° C. for 1 minute, and 72° C for 1 minute; and one cycle at 74° C. for 5 minutes. cDNA products are subjected to nested PCR amplification using sense oligonucleotide primers 95–1202 or 95–88 in combination with either antisense primer 95–89 or 95–656 described in Example 1. PCR conditions are the same as described above. The PCR products are cloned into pCRII using the TA Cloning Kit according to the manufacturer's instructions. The transformants are then screened by extracting plasmid DNA from the transformants using a QIAwell-8 Plasmid Kit (Quiagen, Chatsworth, Calif.) according to the manufacturer's instructions and sequencing the plasmid insert according to the method described in Example 2.

Example 8 Cryptic Intron Identification

The sequenced subclones described in Example 7 fall into three groups and are listed in Table 1 as shown below (FIG. 3, SEQ ID NO:20). The first group contains two deletions designated fragment A and fragment D within the GFP coding sequence. Fragment A, begins at nucleotide 347 with the sequence GTG (ATG nucleotides equal to 1, 2, 3 in GFP coding sequence) and ends at nucleotide 397 with AAG; fragment D, begins at nucleotide 448 with the sequence GTA and ends at nucleotide 503 with TAG. The second group contains a single deletion designated fragment B. Fragment B begins at nucleotide 380 with the sequence GTA and ends at nucleotide 463 with the sequence CAG. The third group also contains a single deletion designated fragment C. Fragment C begins at nucleotide 380 with GTA and ends at nucleotide 503 with TAG. These deleted fragment sequences flanked by the above listed nucleotides, meet the criteria for being recognized as filamentous fungal introns with the expected consensus 5' and 3' splice sites and are likely cryptic introns that have been erroneously spliced from the GFP mRNA in *Aspergillus oryzae*.

TABLE 2

Distribution of Cryptic Introns

| Intron | Number |
|---|---|
| A & D | 15 |
| B | 1 |
| C | 5 |
| D | 3 |

Example 9 Construction of Expression Vector pShTh49

Figure 4B:
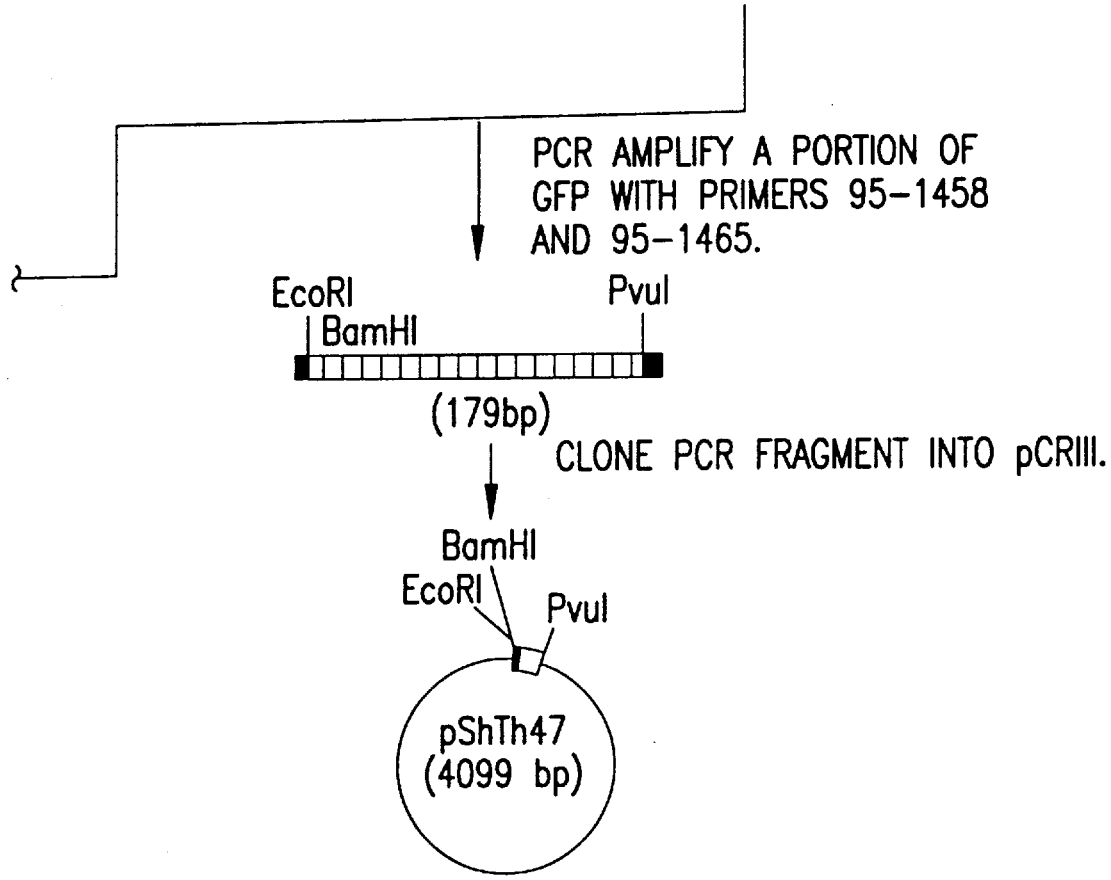
FIG. 4 shows the construction of pShTh49 which includes sequences 95–1411 (SEQ ID NO:7), 95–1412 (SEQ ID NO:8), 95–1413 (SEQ ID NO:9), 95–1414 (SEQ ID NO:10), 95–1415 (SEQ ID NO:11), 95–1422 (SEQ ID NO:12), 95–1457 (SEQ ID NO:13), 95–1458 (SEQ ID NO:14) and 95–1464 (SEQ ID NO:15).
Figure 4D:
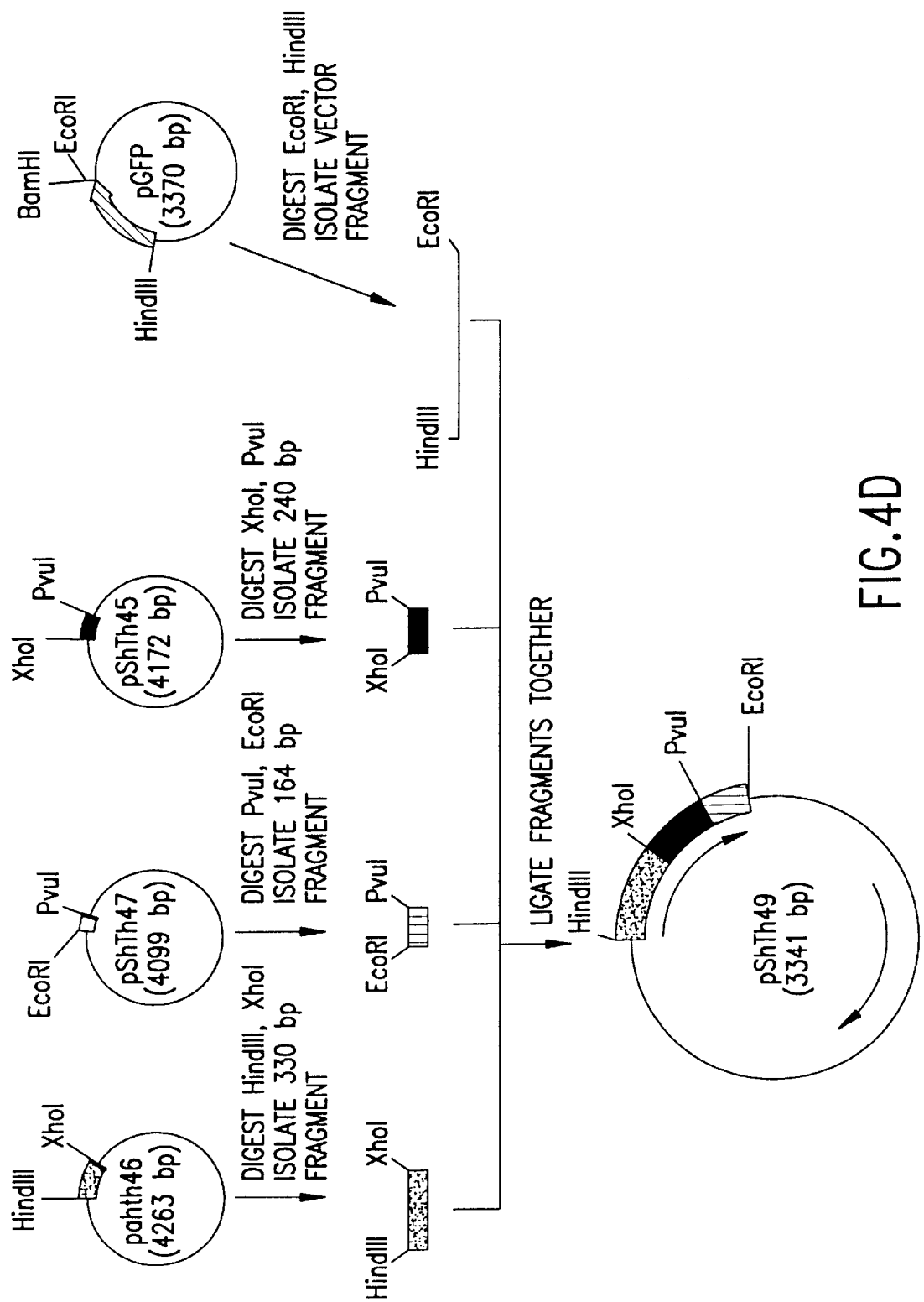

In order to express the GFP gene in an Aspergillus host, the identified putative cryptic splice sites are modified. pShTh49, an *E. coli* expression vector, is constructed to comprise the corrected GFP gene. Specifically, the 5' end of the GFP gene from pUC19-GFP is amplified using the same conditions described in Example 4 with oligonucleotide primers 95–1422 and 95–1457 described in Example 1. Use of these primers introduces a XhoI site 323 bp downstream of the ATG start codon. The fragment is isolated using standard methods of agarose electrophoresis and is then subcloned into pCRII using the TA Cloning Kit (Invitrogen Corp., La Jolla, Calif.) according to the manufacturer's instructions to produce pShTh46. The 3' end of the GFP gene is amplified from pUC19-GFP using the same conditions described in Example 4 with oligonucleotide primers 95–1464 and 95–1458 described in Example 1 to introduce a PvuI site 191 bp upstream of the stop codon. The PCR product is then cloned into pCRII using the TA Cloning Kit according to the manufacturer's instructions to produce pShTh47. The remaining internal coding sequence of GFP, bases 323 to 565 needed for the construction, are synthesized with an Applied Biosystems Model 394 DNA/RNA Synthesizer according to the manufacturer's instructions (Applied Biosystems, Foster City, Calif.) using a codon usage chart for Aspergillus (see Table I, supra). Three-84 base oligonucleotide fragments and a single 50 base oligonucleotide fragment are synthesized (95–1411, 95–1412, 95–1413, and 95–1414), annealed together, and made double stranded with T4 DNA polymerase (Boehringer Mannheim, Indianapolis, Ind.). The resulting fragment is amplified by PCR using the same conditions described in Example 4 with oligomers 95–1414 and 95–1415 described in Example 1. The amplified fragment is isolated using standard methods of agarose electrophoresis and is then cloned into pCRII using the TA Cloning Kit according to the manufacturer's instructions to produce pShTh45. The GFP fragments from pShTh45, pShTh46, and pShTh47 are assembled and the synthetic allele of GFP, gfp49, is introduced into a pUC19 derivative containing the lacZ Shine-Delgarno sequence followed by HindIII, BamHI, EcoRI restriction sites to produce pShTh49 (FIG. 4).

Consequently, changes are made to each of the 5' and 3' splice sites observed in the identified cryptic introns. In addition, throughout the length of the designed fragment, the G+C content is increased whenever possible at the codon wobble positions. Overall, the G+C content of the gene is increased from 38.5% to 44.5% (within the synthetically designed fragment the increase is from 33.3% to 51%). DNA sequencing of the reconstructed gene reveals that base 171, thiamine, is changed to guanine. This single bp change results in a C57W mutation in the protein coding sequence.

Example 10 Transformation of pShTh49 pShTh49 is transformed into *E. coli* DH5α (Bethesda Research Laboratories, Gaithersburg, Md.) according to the manufacturer's instructions and the transformants are observed under a fluorescent microscope as described in Example 3. Transformants are grown at 37° C. with shaking in 5 ml of Luria-Bertani medium supplemented with isopropyl- β-D-thiolgalactopyranoside (IPTG). After 14 hour induction of gfp49 with IPTG, fluorescent *E. coli* are observed with a Zeiss microscope as described in Example 5 showing that gfp49 is a functional protein capable of fluorescing under the same conditions as authentic GFP.

Figure 5:
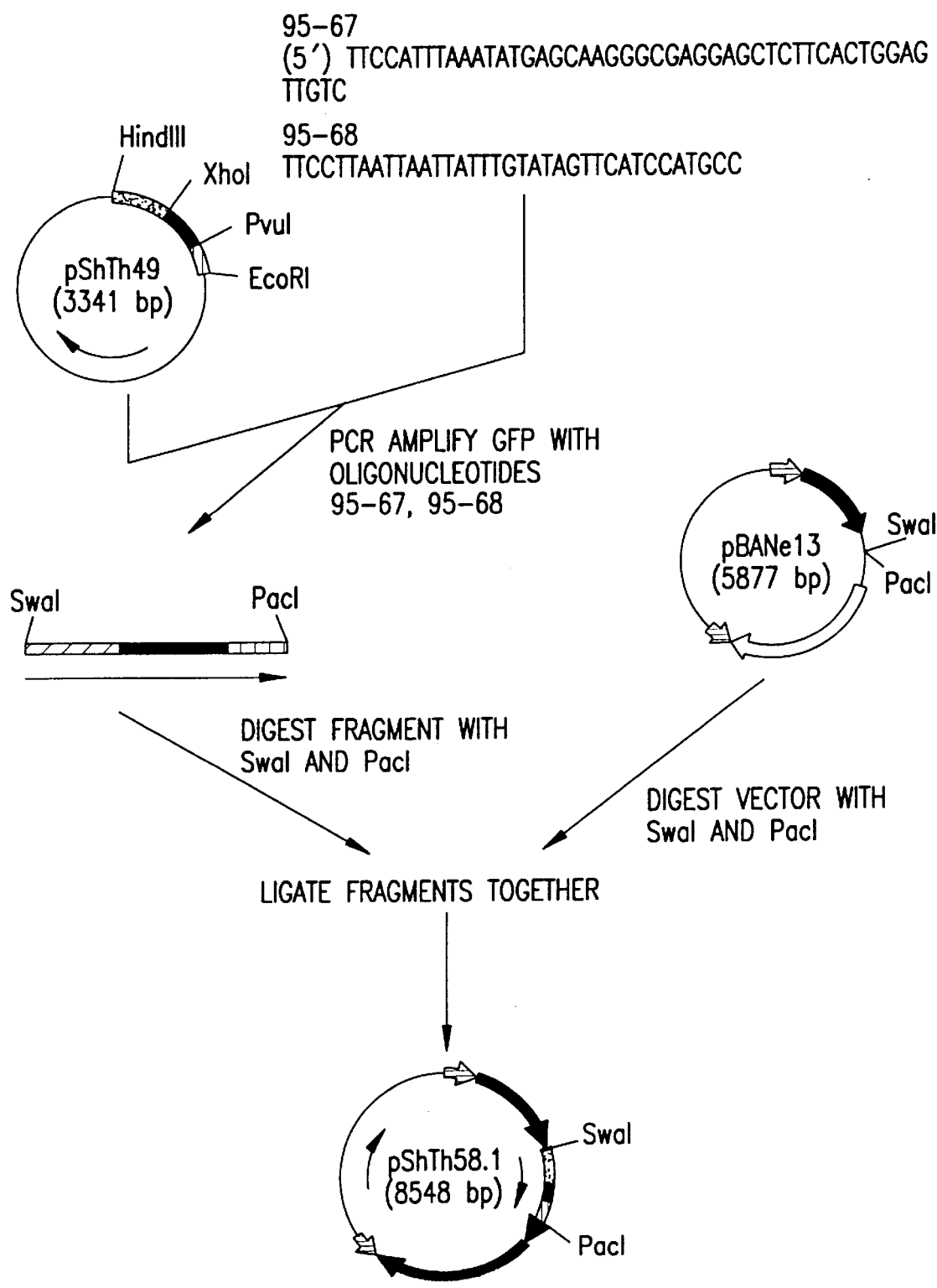
FIG. 5 shows the construction of pShTh58.1 which includes sequences 95–67 (SEQ ID NO:16), 95–68 (SEQ ID NO:17).

Example 11 Construction of Expression Vector pShTh58.1 pShTh58.1, a filamentous fungal expression vector, is constructed first by amplifying a fragment from pShTh49 using the same conditions described in Example 4 with primers 96–67 and 96–68 described in Example 1. The fragment is isolated using standard methods of agarose electrophoresis. The resulting GFP coding fragment contains unique SwaI and PacI restriction sites at the 5' and 3' ends, respectively. This fragment is then digested with SwaI and PacI, isolated using standard methods of agarose electrophoresis, and ligated into pBANel3 vector DNA to produce pShTh58.1 (FIG. 5).

Example 12 Transformation of pShTh58.1 pShTh58.1 is transformed into *Aspergillus oryzae* HowB425 using the same protocol described in Example 5. The resulting transformants are designated ShTh581 strains.

Example 13 Expression of gfp49

Figure 6:
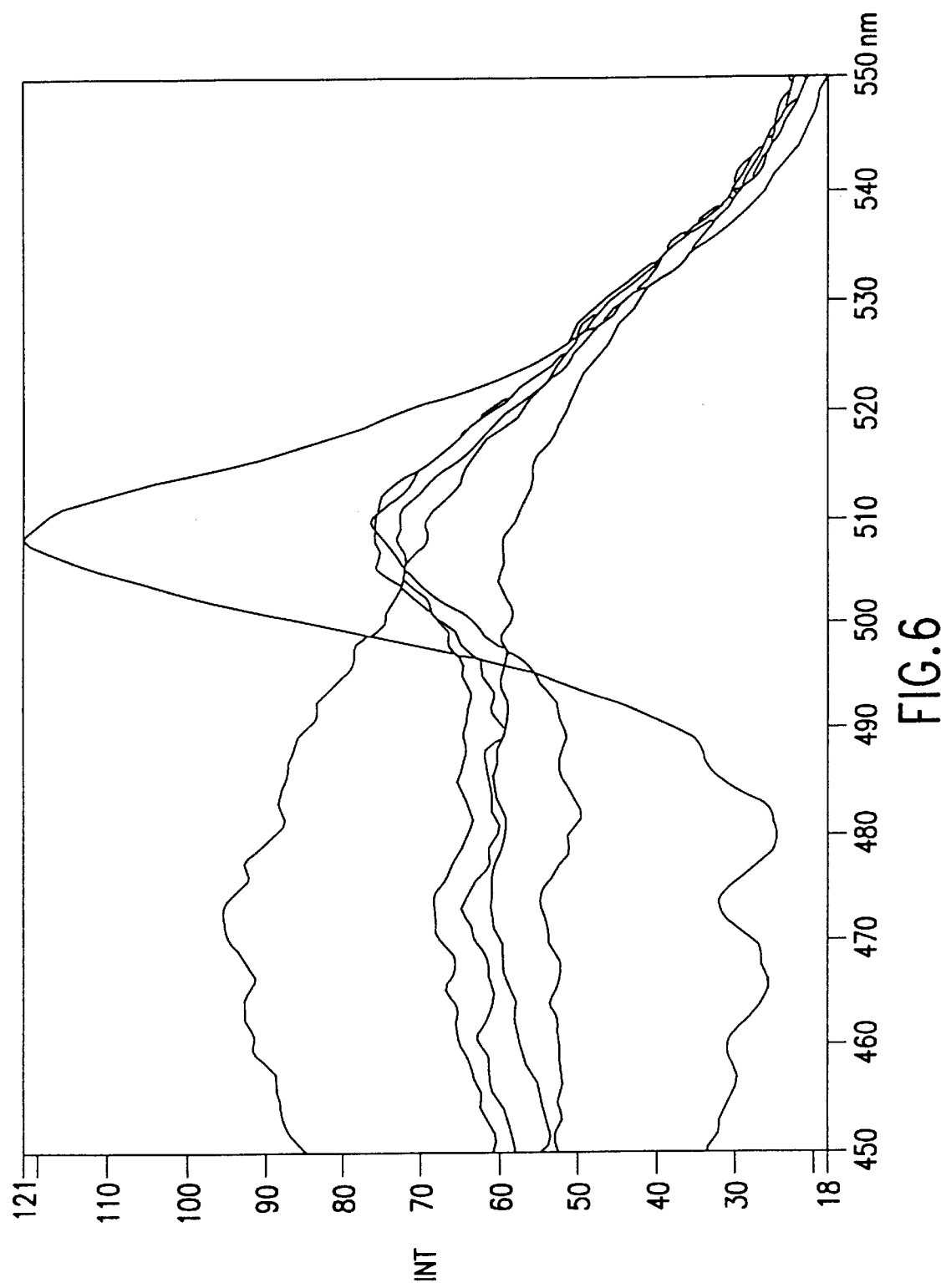
FIG. 6 shows the fluorescence spectrum of GFP produced by transformant ShTh581.1

Five ShTh581 transformants are grown in microtiter plates containing MY51 medium as described in Example 6 to induce the TAKA promoter for GFP production. Mycelia are collected at 3 and 4 days. Intracellular protein from the mycelia is then isolated as described in Example 4 and analyzed for the presence of GFP as described in Example 3. Four of the 5 tested transformnants emit a peak of light corresponding to that of GFP at 509 nm when excited with light of 395 nm (FIG. 6). These results indicate that the corrections in the mRNA of gfp49 result in the correct expression of GFP in *Aspergillus oryzae* which allows for the production of fluorescing GFP.

Example 14 Construction of Expression Vector pShTh58.2

Figure 7:
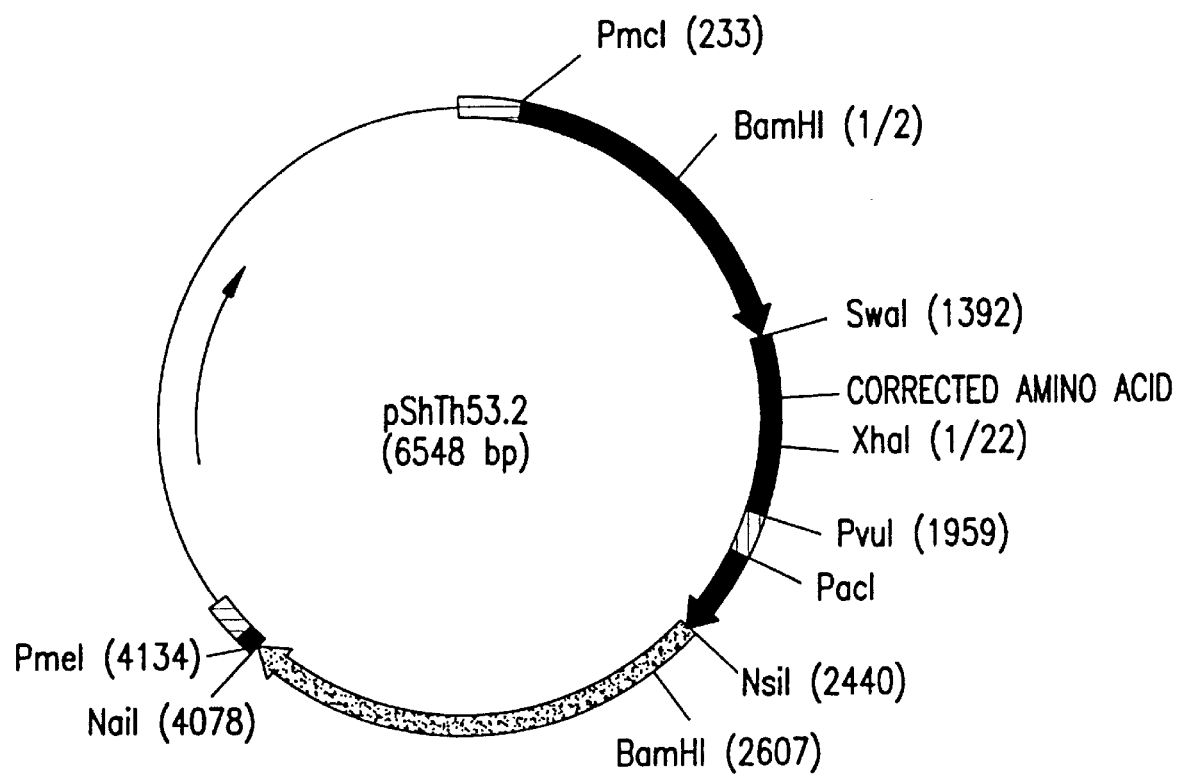
FIG. 7 shows a restriction map of pShTh58.2.

The fungal expression vector pShTh58.2 is constructed by treating pShTh58.1 with the Morph Mutagenesis Kit (5-Prime 3-Prime, Boulder, Colo.). Primer 96–83 is combined with 14 ng of pShTh58.1 according to the manufacturer's instructions to produce pShTh58.2 which corrects the C57W mutation (FIG. 7).

Example 15 Expression of gfp58.2

Figure 8:
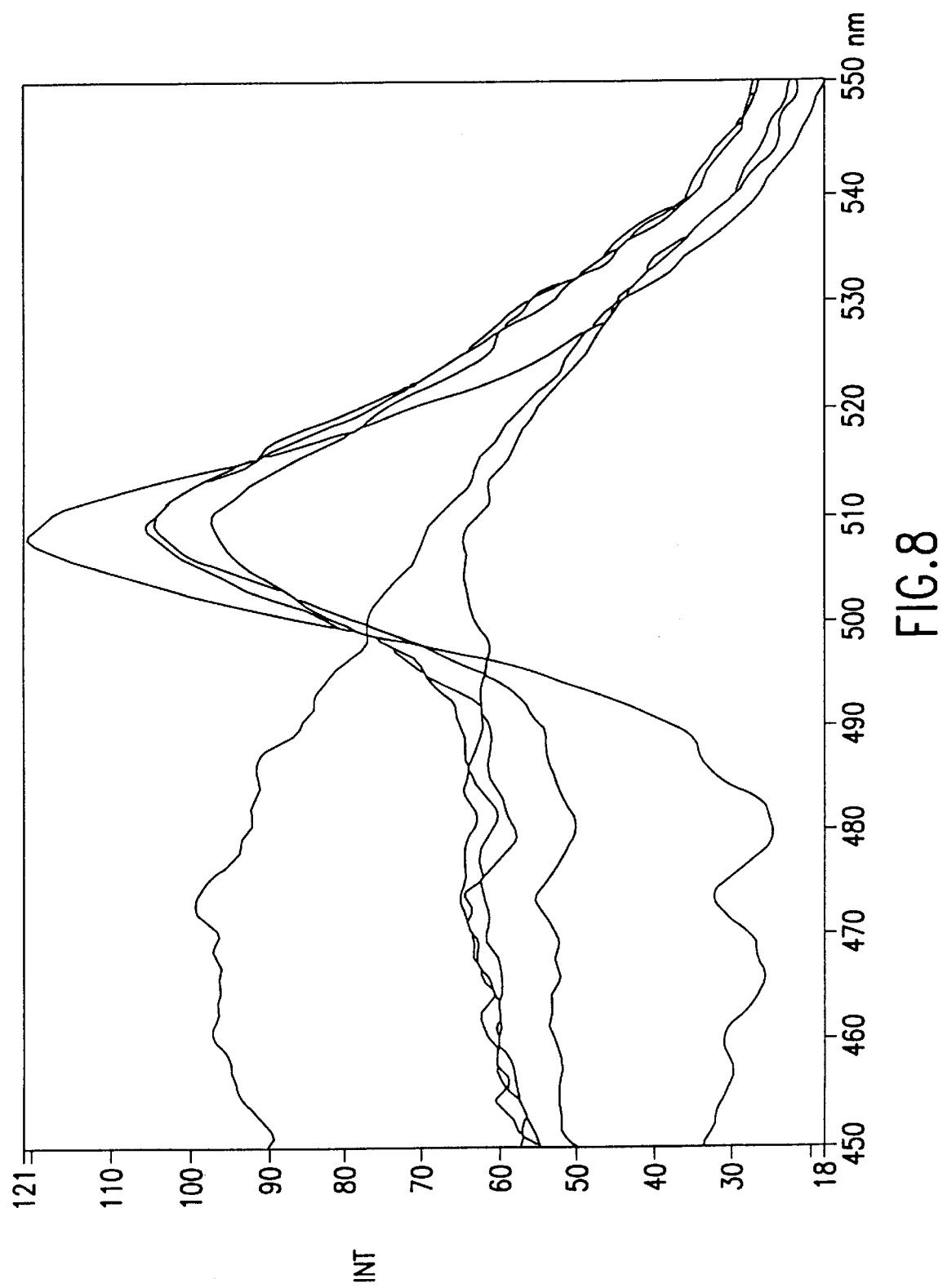
FIG. 8 shows the fluorescence spectrum of GFP produced by transformant ShTh582.1.

One ShTh582 transformant is grown in a microtiter plate containing MY51 media as described in Example 4. Mycelia are collected at 3 and 4 days. Intracellular protein from the mycelia is then isolated as described in Example 4 and analyzed for the presence of GFP as described in Example 6. The transformant is found to produce material which emits a peak fluorescence at 509 nm corresponding to that of GFP when excited with light of 395 nm (FIG. 8). These results indicate that the corrections in the mRNA of gfp49 result in the correct expression of GFP in *Aspergillus oryzae* which allows for the production of GFP.

Example 16 Southern Analysis of GFP Transformants

Spores of transformants ShTh582.1 (GFP with cryptic intron and GC content change) and ShTh581.1 (GFP with cryptic intron and GC content change and 1 amino acid change) as well as ShTh590.1 (wild-type GFP) and BANe130.1 (pBANe13 without GFP) as controls are grown in YEG medium overnight at 37° C. Mycelia are filtered through Miracloth and rinsed three times with distilled water. Extra water is squeezed out. The mycelia are frozen in liquid nitrogen and ground into a fine powder using a mortar and pestle. The Purgene DNA Isolation Kit (Gentra Systems Inc., Research Triangle Park, N.C.) is used to isolate genomic DNA.

Two micrograms of genomic DNA from each sample are digested with PmeI and fractionated by size on a 1% agarose gel. The gel is denatured, neutralized and soaked in 20× SSC for 10 minutes at each step. The digested DNA is transferred for 3 hours onto a nitrocellulose membrane using a Schleicher & Schuell TurboBlotter and the DNA is UV stratalinked. The Boehringer Mannheim Genius System (Boehringer Mannheim, Indianapolis, Ind.) is used to probe the membranes. The membrane is prehybed using Easy Hyb (Boehringer Mannheim, Indianapolis, Ind.) at 42° C. for 1 hour. The GFP probe is DIG labeled using pShTh58.2 DNA, oligonucleotides 96–67 and 96–68, and the Boehringer Mannheim Dig DNA label mix (Boehringer Mannheim, Indianapolis, Ind.). The probe is quantified and added at 1 ng/ml after it is denatured. The membrane is then probed overnight. The probe is decanted and the membrane is washed twice for 5 minutes in 2× SSC-0.1% SDS at room temperature and twice for 15 minutes in 0.1× SSC-0.1% SDS at 65° C. Detection of Dig-labeled nucleotides is done by following the protocol provided by Boehringer Mannheim using Lumi-Phos 530 (Boehringer Mannheim, Indianapolis, Ind.). Membranes are exposed to film for 20 minutes.

The results indicate that GFP bands are observed in the transformants ShTh582.1, ShTh581.1, and ShTh590.1 while no GFP bands are observed in the BANe130.1 transformant.

Deposit of Microorganisms

The following strain has been deposited according to the Budapest Treaty in the Agricultural Research Service Patent Culture Collection (NRRL), Northern Regional Research Laboratory, 1815 University Street, Peoria, Ill. 61604, USA.

| Strains | Accession Number | Deposit Date |
| --- | --- | --- |
| *E. coli* DH5α pShTh58.2 | NRRL B-21584 | June 6, 1996 |

The strain has been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

---

What is claimed is:

1. A method for obtaining a recombinant fungal host cell, which produces a biologically active heterologous polypeptide comprising introducing into a fungal host cell a nucleic acid sequence encoding said heterologous polypeptide, wherein at least one cryptic splice site is modified in the nucleic acid sequence by replacing at least one cryptic consensus sequence of at least one cryptic splice site with a non-consensus sequence or by replacing a first region of a cryptic intron with a second region which has a percent G+C content in the range of about 40% to about 70%, wherein a recombinant fugal host cell which produces a biologically active heterologous polypeptide is obtained.

2. The method according to claim 1, wherein at least one cryptic splice site is modified by replacing a first region comprising at least one cryptic intron or portion thereof with a second region which has a percent G+C content in the range of about 40% to about 70%.

3. The method according to claim 1, wherein at least one cryptic splice site is modified both by replacing at least one cryptic consensus sequence of at least one cryptic splice site with a non-consensus sequence and by replacing a first region of a cryptic intron with a second region which has a percent G+C content in the range of about 40% to about 70%.

4. The method according to claim 1, wherein at least one cryptic splice site is modified by replacing at least one cryptic consensus sequence of at lest one cryptic splice site with a non-consensus sequence.

5. The method according to claim 4, wherein the cryptic consensus sequence is a 5' cryptic consensus sequence.

6. The method according to claim 5, wherein the 5' cryptic consensus sequence is GT, GC, or CT.

7. The method according to claim 6, wherein the 5' cryptic consensus sequence is GTANGT, GCANGT, or CTANGT, wherein N is A, C, G, or T.

8. The method according to claim 4, wherein the cryptic consensus sequence is a 3' cryptic consensus sequence.

9. The method according to claim 8, wherein the 3' cryptic consensus sequence is AG.

10. The method according to claim 8, wherein the 3' cryptic consensus sequence is CAG, TAG, or AAG.

11. The method according to claim 1, wherein the nucleic acid sequence encodes a hormone, an enzyme, a receptor, or a reporter.

12. The method according to claim 11, wherein the nucleic acid sequence encodes a reporter.

13. The method according to claim 12, wherein the reporter is an Aequorea victoria green fluorescent protein.

14. The method according to claim 1, wherein the fungal cell is a filamentous fungal cell.

15. The method according to claim 14, wherein the filamentous fungal cell is a cell of a species of Acremonium, Aspergillus, Fusarium, Humicola, Myceliophthora, Mucor, Neurospora, Penicillium, Thielavia, Tolypocladium, or Trichoderma.

16. A method for producing a biologically active polypeptide comprising
  (a) introducing into a fungal host cell a nucleic acid sequence encoding said biologically active polypeptide, wherein at least one cryptic splice site is modified in the nucleic acid sequence by replacing at least one cryptic consensus sequence of at least one cryptic splice site with a non-consensus sequence or by replacing a first region of a cryptic intron with a second region which has a percent G+C content in the range of about 40% to about70%;
  (b) cultivating the fungal host cell of step (a) in a nutrient medium; and
  (c) recovering said biologically active polypeptide from the nutrient medium of step (b).

17. The method accordig to claim 16, in which said cryptic splice site is modified in the nucleic acid sequence by replacing at least one cryptic consensus sequence of at least one cryptic splice site with a non-consensus sequence and by replacing a first region of a cryptic intron with a second region which has a percent G+C content in the range of about 40% to about 70%.

18. An isolated nucleic acid sequence with at least one cryptic splice site modified by replacing at least one cryptic consensus sequence of at least one cryptic splice site with a non-consensus sequence and/or by replacing a first region of a cryptic intron with a second region which has a percent G+C content in the range of about 40% to about 70%, said nucleic acid sequence encoding a biologically active polypeptide.

19. A nucleic acid construct comprising the nucleic acid sequence of claim 18.

20. A recombinant fungal host cell comprising the nucleic acid construct of claim 19.

21. A recombinant expression vector comprising the nucleic acid construct of claim 19.

22. The vector according to claim 21, wherein the nucleic acid sequence is operably linked to a promoter sequence.

23. The vector according to claim 21, wherein the nucleic acid sequence is operably linked to a transcription termination signal.

24. The vector according to claim 21, further comprising a selectable marker.

25. A recombinant fungal host cell comprising the recombinant vector of claim 21.

* * * * *